United States Patent [19]

Sato et al.

[11] Patent Number: 4,709,024

[45] Date of Patent: Nov. 24, 1987

[54] PRODUCTION OF EPSILON-CAPROLACTAM

[75] Inventors: Hiroshi Sato; Kenichi Hirose, both of Osaka; Norio Ishii, Ehime; Youichi Umada, Osaka, all of Japan

[73] Assignee: Sumitomo Chemical Company, Osaka, Japan

[21] Appl. No.: 896,008

[22] Filed: Aug. 13, 1986

[30] Foreign Application Priority Data

Aug. 28, 1985 [JP] Japan ................................ 60-190593
Feb. 25, 1986 [JP] Japan ................................ 61-40927

[51] Int. Cl.$^4$ .......................................... C07D 201/04
[52] U.S. Cl. ...................................... 540/536; 540/535
[58] Field of Search ................................ 540/535, 536

[56] References Cited

U.S. PATENT DOCUMENTS 3,503,958 3/1970 Landis .................................. 540/335
4,359,421 11/1982 Bell et al. ............................. 540/335
4,472,516 2/1983 Frenken ................................ 502/60

OTHER PUBLICATIONS

Dokl. Akad. Nauk. BSSR 29(10) 924–927 (1985).

Primary Examiner—Robert T. Bond
Attorney, Agent, or Firm—Cushman, Darby & Cushman

[57] ABSTRACT $\epsilon$-caprolactam is prepared by gas phase catalytic synthesis in which cyclohexanone oxime is brought into contact with crystalline alluminosilicate, for example, ZSM-5 H$^+$ form) having 1–12 of constraint index, 500 or more, preferably 1000 or more, of Si/Al atomic ratio and 5$\mu$ equivalent/g or less, preferably 2$\mu$ equivalent/g, of external acid amount.

14 Claims, No Drawings

PRODUCTION OF EPSILON-CAPROLACTAM

FIELD OF THE INVENTION

This invention relates to production of ε-caprolactam, more particularly, the use of a specific crystalline alumino-silicate catalyst in production of ε-caprolactam from cyclohexanone oxime.

BACKGROUND OF THE INVENTION

ε-caprolactam is an important material for nylon and the like. One of processes for preparing said caprolactam is liquid-phase catalytic rearrangement of cyclohexanone oxime in the presence of sulfuric acid. Alternatively, gas-phase catalytic rearrangements in the presence of solid acid are proposed, e.g., boric acid compounds (Japanese published unexamined patent application Nos. 37686/1978 and 12125/1971), silica-alumina (British Pat. No. 881927), solid phosphoric acid (British Pat. No. 881926), mixed metal oxides (Journal of the Chemical Society of Japan, No. 1, 77, 1977), Y-zeolite (Journal of Catalysis, 6, 247, 1966) and crystalline aluminosilicate (Japanese published unexamined patent application No. 139062/1982).

Problems encountered are use of a large amount of fuming sulfuric acid, a large amount of ammonium sulfate by-produced and corrossion of apparatuses caused by fuming sulfuric acid, when sulfuric acid is used above. There are no such problems in the alternative processes above in which solid acid is used. However, they have the other difficulties in reaction selectivity of ε-caprolactam, life of catalyst, production yield per catalyst, conversion rate of oxime etc. For instance, Japanese published unexamined patent application No. 139062/1982 where crystalline alumino-silicate e.g. ZSM-5 having 40-60 of Si/Al atomic ratio is used discloses no selectivity of ε-caprolactam but that conversion rate of cyclohexanone oxime is said to be quantitative in such a case where weight hourly space velocity (hereinafter referred to as "WHSV") is as low as about 2.5 hr$^{-1}$ and life of catalyst is as short as 15-20 hours. The present inventors have repeated the process of the Japanese published unexamined patent application mentioned above to confirm shortness of life of catalyst and low selectivity of ε-caprolactam, particularly too short life of catalyst and too small selectivity under commercial WHSV, for example, about 10 hr$^{-1}$ or higher.

SUMMARY AND OBJECTS OF THE INVENTION

The present inventors have studied production of ε-caprolactam using a crystalline alumino-silicate catalyst having a constraint index of 1-12 until it was found that alumino-silicate having specific Si/Al atomic ratio and specific acid amount of external surface greatly improves conversion rate of oxime, selectivity of lactam, life of catalyst, and productivity.

DESCRIPTION OF THE INVENTION

According to the present invention, in production ε-caprolactam by gas-phase catalytic rearrangement of cyclohaxanone oxime in the presence of crystalline alumino-silicate having constraint index of 1-12, an improvement in the crystalline catalyst is provided wherein Si/Al atomic ratio is not smaller than 500 and an acid amount of external surface is not greater than 5μ equivalent/g. It is beyond expectation that an aluminosilicate catalyst having such high silica content as well as low acidity as defined above with respect to Si/Al atomic ratio and acid amount of external surface displays high catalytic performance (oxime conversion rate), in view of teaching that such a catalyst is hardly workable (Journal of Catal. 61, 393, 1980). Furthermore, the present catalyst greatly improves selectivity of lactam, life of catalyst and productivity, over a catalyst having not higher than 100 of Si/Al atomic ratio, which is familiar to the skilled in the art.

Constraint index means degree of controlling access of molecules having larger sectional area than n-hexane by pore structure of crystalline alumino-silicate and is defined by the formula given below:

$$\text{Constraint index} = \frac{\log_{10}(\text{remaining n-hexane})}{\log_{10}(\text{remaining 3-methylpentane})}$$

An outline is that a mixture of n-hexane and 3-methylpentane having different effective molecular diameters is brought into contact under specific conditions with an alumino-silicate catalyst to cause cracking reaction and the constraint index is calculated on the basis of reaction ratio. Values somewhat vary depending on experiment conditions. The average value is taken, after experiment is made under various conditions. Details is given in Japanese published unexamined patent application No. 133223/1981.

Crystalline alumino-silicate having 1-12 of constraint index includes "Nu zeolite", "EU zeolite" manufactured by ICC, (Catalysis Reviews—Science & Engineering 27, 461, 1985), "ZBM zeolite" manufactured by BASF (West Germany Pat. Nos. 2830787 (1980) and 3006471 (1981)), "TPZ zeolite" manufactured by Teijin Yuka Co. Ltd., Japanese published unexamined patent application Nos. 95281/1982 and 149819/1982) in addition to "ZSM zeolite" manufactured by Mobile Oil Co. and "Silicalite" manufactured by U.C.C.. Examples are "ZSM-5" [constraint index: 8.3 (hereinafter, terms "Constraint index" are omitted), Japanese published unexamined patent application No. 10064/1971], "ZSM-11" (8.7, Japanese published examined patent application No. 23280/1978), "ZSM-12" (2, Japanese published examined patent application No. 16079/1977), "ZSM-23" (9.1, Japanese published examined patent application No. 149900/1976), "ZSM-35" (4.5, Japanese published unexamined patent application No. 144500/1978), "ZSM-38" (2, U.S. Pat. No. 4,046,859), "ZSM-48" (3.4, Japanese published unexamined patent application No. 133223/1981) and "Silicalite" (8.5, U.S. Pat. No. 4,061,724). X-ray patterns and preparing processes thereof are disclosed in the respective literatures. Preferred are "ZSM-5" and "Silicalite".

The present catalyst additionally satisfies two more parameters, i.e., 500 or more, preferably 1000 or more of Si/Al atomic ratio and 5μ equivalent/g or less, preferably 2μ equivalent/g or less of acid amount of external surface. These limits are critical. Si/Al atomic ratio is calculated on the basis of atomic adsorption spectroscopy after crystallinity is measured by, for example, X-ray and then exact elemental analysis of Si and Al in crystal skeleton is made. Another approach for Si/Al atomic ratio in the skeleton is from $^{29}$Si signal in MAS-NMR spectrum. Acid amount of external surface is calculated from an adsorption amount of 4-methylquinoline (Journal of Petroleum Chemical Society of Japan, 25, 69, 1982; Journal of Catal. 58, 114, 1979).

Generally speaking, particularly in a high silica region as in the present invention, crystallinity as well as crystal growth increase while external surface area decreases as Si/Al atomic ratio increases. The greater the external surface area is, the better the catalytic activity and selectivity are. Preferred is 5 m²/g or more. The external surface area is observed by a porefilling up process, i.e., pores in the crystal are filled up with organic or inorganic molecules and then the necessary surface area is observed by BET method on the basis of an adsorption amount of nitrogen or krypton adsorbed onto the external surface. The molecules used to fill up the pores are organic ones such as butane, hexane, benzene and the like, water (7th and 8th Seminars on catalysts, Catalyst Society, Japan, 1984 and 1985) and organic amines, tetra-alkylammónium cation used as a crystallization-controlling agent in hydrothermal synthesis. For example, hydrothermal synthesis of crystalline alumino-silicate in which constraint index is 1–12 and Si/Al atomic ratio is 500 or more, is effected in the presence of, usually, organic amines or tetra-alkylammonium cation as a crystallization-controlling agent which exists in a filler for pores just when the synthesis is finished. BET surface area of zeolite is external surface area, said zeolite having been dried at a temperature up to 120° C. immediately after the synthesis is finished.

The crystalline alumino-silicate catalyst having high silica content and low acidity mentioned above may be selected from crystalline alumino-silicates prepared by processes disclosed in Japanese published unexamined patent application No. 164617/1984 or U.S. Pat. No. 4,061,724. A Si-source for preparing the compounds should be as pure as possible having a greatly small amount of Al impurity, e.g., tetraalkyl ortho-silicate, aerogel, colloidal silica, sodium silicate (JIS Grade No. 3 of water glass).

Alumino-silicate obtained from hydrothermal synthesis should be calcined in air until organic amine cation is removed, subjected to ion-exchange with aqueous ammonium chloride solution or diluted aqueous hydrochloric acid solution and calcined again until it is converted to the H+ form, since the silicate usually contains organic amine cation used as a crystallization-controlling agent and alkali metal cations such as Na+, K+. Alternatively, the corresponding polyvalent metal ion form may be used in place of the H+ form, wherein the ion-exchange is effected by use of aqueous alkaline earth metal solution containing, for example, $Ca^{2+}$, $Mg^{2+}$, $Sr^{2+}$ and $Ba^{2+}$, or aqueous lanthanoide series solution containing, for example, $La^{2+}$ and $Ce^{3+}$ in place of the aqueous ammonium chloride or diluted hydrochloric acid solution.

Gas phase catalytic reaction is carried out in a fixed-bed or flow-layer operation. Cyclohexanone oxime, the starting compound, is vaporized in a vaporizer and then is brought in the gas form into contact with a catalyst. The cyclohexanone oxime may be fed alone, but preferably in the form of solution in benzene or toluene to the vaporizer. In the latter case, the solution may be carried by an inert carrier gas such as $N_2$, $CO_2$ etc. Preferred is $CO_2$ gas, since selectivity of lactam is improved.

Reaction temperature is usually 250°–500° C., preferably 300°–450° C. Feeding speed (WHSV) is 0.1–100 $hr^{-1}$, preferably 1–50 $hr^{-1}$, more preferably 5–40 $hr^{-1}$.

Regeneration of catalyst whose activity falls down after a long use is effected by calcining at 450°–550° C. in air stream.

Isolation of ε-caprolactam is effected by, for example, cooling and condensing a reaction gas and then distilling or recrystallizing.

In accordance with the present process, conversion rate of cyclohexanone oxime and selectivity of ε-caprolactam are greatly improved, an amount of carbon deposition on a catalyst is very small, life of catalyst is greatly prolonged and high yield of ε-caprolactam is secured for a long period of time. Furthermore, high productivity per catalyst is attained with high WHSV. Recovery of activity is easily made by calcining a used catalyst in air. Repeated use of catalyst is possible.

REFERENCE EXAMPLE 1

(Synthesis of high silica H.ZSM-5)

"Aerozil" (trade name, manufactured by Japan Aerozil Co. Ltd., Al≦8.8 ppm, 26 g), colloidal silica (manufactured by Shokubai Kasei, Co. Ltd., Japan, ST-30, $SiO_2$=30%) (200 g), distilled water (230 g) and aqueous solution (250 g) containing tetra-n-propylammonium bromide (34 g) were charged in an autoclave (1.5 l) made of SUS, and the content was vigorously stirred. Aqueous solution (100 g) containing sodium hydroxide (7.4 g) was charged at one time and the mixture was vigorously stirred for 30 min. The autoclave was tightly sealed, and then dipped in an oil bath until inner temperature reached 190° C. Stirring (400 r.p.m.) was continued for 72 hours keeping the temperature as above. Pressure within the autoclave reached 16 Kg/cm² from 14 Kg/cm². PH at the end of hydrothermal synthesis was 11.8. White solid produced was separated by filtration. Product was continuously washed with distilled water until pH of filtrate reached about 7. Product was dried at 120° C. for 16 hours. BET surface of crystal at that stage was observed by a nitrogen gas adsorption method to obtain 1.4 m²/g of external surface area.

The crystal dried was calcined in air stream at 500°–530° C. for 4 hours to obtain 80 g of powdery white crystals.

By powder X ray diffraction assay, ZSM-5 was identified.

Si/Al atomic ratio=2,950 (atomic absorption spectroscopy assay.)

To the crystals (10 g) was added 5% aqueous NH₄Cl solution (100 g) and then the mixture was subjected to ion-exchange at 50°–60° C. for one hour before filtration. The ion-exchange treatment was repeated four times. Crystals were washed with distilled water until no Cl⁻ was detected. Crystals were dried at 120° C. for 16 hours. Crystals (NH₄ form) were shaped to particles (24–48 mesh in size) and calcined at 500° C. for 4 hours to obtain ZSM-5 (H form, hereinafter referred to as "H.ZSM-5").

Surface acidity (pKa)= −3 (an indicator assay).

An adsorption amount of 4-methylquinoline (which is referred to as 4 MQ hereinafter) at 350° C.=0.22μ equivalent/g.

EXAMPLE 1

(A test under high WHSV)

H.ZSM-5 (0.3 g, 0.5 ml, 24–48 mesh in size), a catalyst, prepared in Reference example above was packed in a reactor made of quartz (32 cm long, 1 cm inner diameter) and $N_2$ gas was flowed at 350° C. for one hour. After the pre-treatment, 8 wt.% cyclohexanone/benzene solution was fed (WHSV=38.5 $hr^{-1}$) from a vaporizer. Temperature of the catalyst layer was 350° C. Reaction product was trapped and collected under water-cooling. Gas-chromatography [column: 20% silicone SE-30/chromosorb AW-DMCS (60/80 M) 2 m: glass column, internal standard pseudocumene] gave the result shown in Table 1.

| time elapsed (hr) | cyclohexanone oxime conversion (%) | ε-caprolactam yield (%) | ε-caprolactam selectivity (%) |
| --- | --- | --- | --- |
| 1.3 | 73.8 | 53.2 | 72.2 |
| 2.3 | 49.4 | 36.5 | 73.5 |
| 3.3 | 37.2 | 27.4 | 73.7 |
| 4.3 | 30.3 | 22.8 | 75.2 |
| 5.3 | 26.3 | 19.6 | 74.5 |
| 6.3 | 24.4 | 17.4 | 71.1 |

REFERENCE EXAMPLE 2

(Synthesis of highly pure "Silicalite")

"Silicalite" was prepared referring to U.S. Pat. No. 4,061,724. "Aerozil" (manufactured by Japan Aerozil Co. Ltd., Al≦8.8 ppm, 70 g), distilled water (600 g) and aqueous solution (156 g) containing tetra-n-propylammonium bromide (36 g) were charged in an autoclave (1.5 l) made of SUS, and the content were vigorously stirred. An aqueous solution (60 g) containing sodium hydroxide (7.8 g) was added at a time and the mixture was vigorously stirred for 30 min. The autoclave was tightly sealed and dipped in an oil bath until the inner temperature reached 190° C. Stirring (400 r.p.m.) was continued for 72 hours at that temperature until the pressure in the autoclave rose from 14 Kg/cm$^2$ to 16 Kg/cm$^2$. The steps of calcining-ion exchange with aqueous NH$_4$Cl solution-calcining were effected in the same manner as in Reference example 1, to obtain "Silicalite".

Si/Al atomic ratio=25,000
4-MQ adsorption amount=0.01μ equivalent/g
External surface area=1.5 m$^2$g,
Surface acidity=from −3.0 to +4.8

EXAMPLE 2

(A test under high WHSV)

Example 1 was repeated except that a catalyst used was "Silicalite" (0.3 g, 0.5 ml, 24–48 mesh in size) prepared by Reference example 2 in place of the H.ZSM-5. Result is shown in Table 2.

| time elapsed (hr) | cyclohexanone oxime conversion (%) | ε-caprolactam yield (%) | ε-caprolactam selectivity (%) |
| --- | --- | --- | --- |
| 1.3 | 65.4 | 44.0 | 67.3 |
| 2.3 | 55.9 | 41.2 | 73.7 |
| 3.3 | 53.9 | 38.4 | 71.3 |
| 4.3 | 50.7 | 35.7 | 70.5 |
| 5.3 | 46.7 | 34.0 | 72.9 |
| 6.3 | 45.5 | 31.8 | 69.8 |
| 7.3 | 43.5 | 31.1 | 71.5 |

REFERENCE EXAMPLE 3

(Synthesis of high silica H.ZSM-5)

To an autoclave (1.5 l) made of SUS were charged Si(OEt)$_4$ (90 g, manufactured by Hani Chemical Co. Ltd, Japan) containing aqueous 20–25% tetra-n-propylammonium hydroxide solution (130 g), ethanol (60 g) and H$_2$O (100 g). Colloidal silica (SI-30) (200 g, manufactured by Shokubai Kasei Co. Ltd., Japan) was added to the content in the autoclave at a time under vigorous stirring. Vigorous stirring was continued for 30 min. after the addition. The autoclave was tightly sealed and dipped in an oil bath until temperature reached 160° C. Stirring (400 r.p.m.) was continued for 120 hours at that temperature until pressure reached 9.5–11 Kg/cm$^2$. As same as Reference example 1, steps of drying—calcining—ion exchange with aqueous NH$_4$Cl solution—calcining were effected to obtain H.ZSM-5.

Si/Al atomic ratio=2410
4 MQ adsorption amount≃0μ equivalent/g
Surface acidity pKa=−3.0
External surface area=3.0 m$^2$/g

EXAMPLE 3

(A test under high WHSV)

Example 1 was repeated to effect rearrangement of cyclohexanone oxime except that a catalyst used was H.ZSM-5 prepared by Reference example 3, in place of the H.ZSM-5.

Result is shown in Table 3.

TABLE 3

| time elapsed (hr) | cyclohexanone oxime conversion (%) | ε-caprolactam yield (%) | ε-caprolactam selectivity (%) |
| --- | --- | --- | --- |
| 1.3 | 70.7 | 43.4 | 61.4 |
| 2.3 | 53.3 | 36.1 | 67.8 |
| 3.3 | 44.6 | 31.4 | 70.3 |
| 4.3 | 39.0 | 27.0 | 69.4 |
| 5.3 | 37.0 | 23.7 | 64.1 |
| 6.3 | 34.1 | 21.0 | 61.4 |

REFERENCE EXAMPLE 4

(Synthesis of high silica H.ZSM-5)

ZSM-5 was synthesized referring to Japanese published unexamined patent application No. 164617/1984. That is, to an autoclave (1.5 l) made of stainless-steel, were charged tetra-ethylortho-silicate [Si(OEt)$_4$, 100 g, Al<10 ppm], aqueous 10% tetra-n-propylammonium hydrochloride solution (224 g) and ethanol (60 g) and the content was stirred well. To this was added aqueous aluminium sulfate solution (48 g) (Al$_2$(SO$_4$)$_3$.16H$_2$O, 62 mg/48 g of water) and the mixture (pH 12.4) was stirred vigorously for 30 min. The autoclave was tightly sealed and dipped in an oil bath until temperature reached 160° C. Hydrothermal synthesis was conducted for 120 hours at that temperature with stirring (at least 400 r.p.m.), until pressure reached 14 Kg/cm$^2$ from 12 Kg/cm$^2$ and pH was 11.7. White solid product was filtered and continuously washed with distilled water until pH of filtrate was about 7. The product was dried at 120° C. for 16 hours. BET surface area of crystals was 4.9 m$^2$/g in terms of external surface area (nitrogen gas adsorption assay). The crystals dried were calcined at 500°–530° C. for 4 hours in air stream to obtain powdery white crystals (27 g). These were identified as ZSM-5 (powder X ray diffraction).

Si/Al atomic ratio=2,290 (atomic absorptiometry)
To 10 g of these crystals was added aqueous 5% NH$_4$Cl solution (100 g) to carry out ion-exchange at 50°–60° C. for one hour, before filtration. The ion-exchange step was repeated four times. Crystals were washed with distilled water until no Cl$^-$ was detected, before they were dried at 120° C. for 16 hours. Crystals (NH₄ form) were shaped to particles (24–48 mesh in size) and calcined at 500° C. for 4 hours to convert to H.ZSM-5.

Surface acidity pKa=−3 (an indicator assay)

4-MQ adsorption amount at 350° C.=2.23μ equivalent/g.

EXAMPLE 4

Example 1 was repeated except that catalyst used was H.ZSM-5 prepared in Reference example 4 in place of the H.ZSM-5.

Result is shown in Table 4.

TABLE 4

| time elapsed (hr) | cyclohexanone oxime conversion (%) | ε-caprolactam yield (%) | ε-caprolactam selectivity (%) |
|---|---|---|---|
| 1.3 | 72.3 | 45.3 | 62.7 |
| 2.3 | 63.4 | 38.3 | 60.4 |
| 3.3 | 58.4 | 35.1 | 60.1 |
| 4.3 | 54.8 | 33.7 | 61.5 |
| 5.3 | 52.4 | 32.2 | 61.4 |
| 6.3 | 50.9 | 29.8 | 58.6 |

REFERENCE EXAMPLE 5

(Synthesis of high silica H.ZSM-5)

Reference example 4 was repeated to effect hydrothermal synthesis except that amount of aluminium sulfate was changed as in Table 5. Through calcining—ion-exchange with NH₄Cl—calcining, H.ZSM-5s having Si/Al atomic ratios as in Table 6 were obtained.

TABLE 5

| No. | Si(OEt)₄ | Al₂(SO₄)₃·16 H₂O(g) | pH when charged | pH when finished | Si/Al ratio when charged |
|---|---|---|---|---|---|
| 1 | 100 | 0.078 | 13.0 | 11.8 | 2,000 |
| 2 | 100 | 0.031 | 12.8 | 11.3 | 5,000 |
| 3 | 100 | 0.125 | 12.6 | 12.2 | 1,250 |

TABLE 6

| No. | Si/Al (atomic ratio) | 4MQ adsorption amount (μ equivalent/g) | Surface acidity (pKa) | External surface area (m²/g) |
|---|---|---|---|---|
| 1 | 2,017 | 0.84 | −3.0 | 9.2 |
| 2 | 3,930 | 0.36 | −3.0 | 5.7 |
| 3 | 1,160 | 0.06 | −3.0 | 5.8 |

EXAMPLES 5–7

(Tests under high WHSV)

Example 1s were repeated except that catalysts used were H.ZSM-5 Nos. 1–3 prepared in Reference example 5, respectively, in place of the H.ZSM-5.

Results are shown in Tables 7–9.

TABLE 7

(No. 1 catalyst)

| time elapsed (hr) | cyclohexanone oxime conversion (%) | ε-caprolactam yield (%) | ε-caprolactam selectivity (%) |
|---|---|---|---|
| 2.3 | 99.3 | 71.8 | 72.3 |
| 3.3 | 98.1 | 71.7 | 73.1 |
| 4.3 | 96.2 | 70.6 | 73.4 |
| 5.3 | 94.2 | 67.5 | 71.6 |
| 6.3 | 91.7 | 65.1 | 71.0 |

TABLE 8

(No. 2 catalyst)

| time elapsed (hr) | cyclohexanone oxime conversion (%) | ε-caprolactam yield (%) | ε-caprolactam selectivity (%) |
|---|---|---|---|
| 1.3 | 98.7 | 65.1 | 66.0 |
| 2.3 | 93.3 | 66.7 | 71.4 |
| 3.3 | 85.5 | 59.5 | 69.6 |
| 4.3 | 78.3 | 56.2 | 71.8 |
| 5.3 | 71.2 | 52.2 | 73.3 |
| 6.3 | 64.7 | 48.3 | 74.5 |
| 7.3 | 60.3 | 42.8 | 71.0 |

TABLE 9

(No. 3 catalyst)

| time elapsed (hr) | cyclohexanone oxime conversion (%) | ε-caprolactam yield (%) | ε-caprolactam selectivity (%) |
|---|---|---|---|
| 1.3 | 98.4 | 67.9 | 69.1 |
| 2.3 | 93.8 | 67.6 | 72.1 |
| 3.3 | 88.0 | 64.5 | 73.3 |
| 4.3 | 81.8 | 60.1 | 73.5 |
| 5.3 | 74.9 | 59.4 | 79.3 |
| 6.3 | 70.5 | 53.2 | 75.6 |
| 7.3 | 67.3 | 48.3 | 71.7 |

EXAMPLE 8

(A test under high WHSV)

Example 5 was repeated except that the catalyst used therein was calcined in a reactor at 500° C. for 3 hours in air stream, in place of the H.ZSM-5.

Result is shown in Table 10.

TABLE 10

| time elapsed (hr) | cyclohexanone oxime conversion (%) | ε-caprolactam yield (%) | ε-caprolactam selectivity (%) |
|---|---|---|---|
| 1.3 | 100 | 71.0 | 71.0 |
| 2.3 | 99.5 | 71.6 | 72.0 |
| 3.3 | 98.0 | 71.1 | 72.5 |
| 4.3 | 96.0 | 69.0 | 72.0 |
| 5.3 | 94.1 | 67.6 | 71.8 |
| 6.3 | 92.0 | 66.5 | 72.3 |

REFERENCE EXAMPLE 6

(Synthesis of metal ion-exchanged ZSM-5)

ZSM-5s (NH₄ form) obtained in Reference example 5, No. 1 (4 g each) were subjected four times, at 90° C. for one hour each, to ion-exchange treatment with aqueous 5% solution (50 ml each) containing metal salts (MXn: X=Cl⁻ or OAc⁻) shown in Table 11. After washing with water, drying and calcining, metal ion-exchanged ZSM-5s were obtained.

TABLE 11

| Run No. | Metal salts | M.ZSM-5 |
|---|---|---|
| 1 | Ca(OAc)₂ | Ca.ZSM-5 |
| 2 | Sr(OAc)₂ | Sr.ZMS-5 |

EXAMPLES 9-11

(Tests under high WHSV)

Example 1s were repeated except the metal ion-exchanged ZSM-5s prepared in Reference example 6 were used in place of H.ZSM-5s in Example 5. Results are shown in Tables 12-14.

TABLE 11-continued

| Run No. | Metal salts | M.ZSM-5 |
|---|---|---|
| 3 | LaCl$_3$ | La.ZSM-5 |

TABLE 12

(Ca.ZSM-5)

| time elapsed (hr) | cyclohexanone oxime conversion (%) | ε-caprolactam yield (%) | ε-caprolactam selectivity (%) |
|---|---|---|---|
| 1.3 | 100 | 72.0 | 72.0 |
| 2.3 | 99.0 | 73.3 | 74.0 |
| 3.3 | 98.1 | 70.9 | 72.3 |
| 4.3 | 96.0 | 67.7 | 70.5 |
| 5.3 | 94.0 | 69.0 | 73.0 |
| 6.3 | 90.2 | 65.8 | 73.0 |

TABLE 13

(Sr.ZMS-5)

| time elapsed (hr) | cyclohexanone oxime conversion (%) | ε-caprolactam yield (%) | ε-caprolactam selectivity (%) |
|---|---|---|---|
| 1.3 | 100 | 70.3 | 70.3 |
| 2.3 | 100 | 70.5 | 70.5 |
| 3.3 | 100 | 71.0 | 71.0 |
| 4.3 | 99.3 | 72.3 | 72.8 |
| 5.3 | 98.1 | 70.6 | 72.0 |
| 6.3 | 96.0 | 67.8 | 70.6 |

TABLE 14

(La.ZSM-5)

| time elapsed (hr) | cyclohexanone oxime conversion (%) | ε-caprolactam yield (%) | ε-caprolactam selectivity (%) |
|---|---|---|---|
| 1.3 | 99.0 | 69.3 | 70.0 |
| 2.3 | 98.1 | 69.8 | 71.2 |
| 3.3 | 97.0 | 69.2 | 71.3 |
| 4.3 | 96.2 | 69.6 | 72.4 |
| 5.3 | 94.0 | 67.2 | 71.5 |
| 6.3 | 91.0 | 64.3 | 70.7 |

REFERENCE EXAMPLE 7

Reference example 4s were repeated except that the hydrothermal synthesis was effected using aluminium sulfate and temperature shown in Table 15 to obtain H.ZSM-5 shown in Table 16.

TABLE 15

| No. | Al$_2$(SO$_4$)$_3$·16H$_2$O (mg) | temperature |
|---|---|---|
| 1 | 98 | 105 |
| 2 | 70 | 160 |
| 3 | 54 | 130 |
| 4 | 0 | 105 |

TABLE 16

| No. | Si/Al atomic ratio | 4MQ adsorption amount (μ equivalent/g) | Surface acidity (pKa) | External surface area (m$^2$/g) |
|---|---|---|---|---|
| 1 | 1,600 | 3.92 | −3.0 | 10.3 |
| 2 | 2,240 | 2.01 | −3.0 | 7.3 |
| 3 | 2,900 | 0.35 | −3.0 | 8.7 |
| 4 | 27,000 | *1 | *2 | 11.7 |

Notes:
*1 = zero
*2 an indicator (pKa = −3, dicinnamylacetone) is slightly coloured

EXAMPLES 12-14

(Tests under high WHSV)

Example 1s were repeated except H.ZSM-5, Nos. 1-3 prepared in Reference example 7 were employed, respectively, in place of the H.ZSM-5.
Results are shown in Tables 17-19.

TABLE 17

(No. 1 catalyst of Reference example 7)

| time elapsed (hr) | cyclohexanone oxime conversion (%) | ε-caprolactam yield (%) | ε-caprolactam selectivity (%) |
|---|---|---|---|
| 1.3 | 99.0 | 72.1 | 72.9 |
| 2.3 | 97.7 | 74.6 | 76.4 |
| 3.3 | 96.1 | 77.4 | 80.5 |
| 4.3 | 94.1 | 77.7 | 82.6 |
| 5.3 | 92.5 | 74.3 | 80.3 |
| 6.3 | 90.9 | 73.0 | 80.0 |

TABLE 18

(No. 2 catalyst of Reference example 7)

| time elapsed (hr) | cyclohexanone oxime conversion (%) | ε-caprolactam yield (%) | ε-caprolactam selectivity (%) |
|---|---|---|---|
| 1.3 | 99.5 | 83.4 | 84.8 |
| 2.3 | 98.3 | 82.7 | 84.1 |
| 3.3 | 98.0 | 82.0 | 83.6 |
| 4.3 | 96.9 | 83.4 | 86.1 |
| 5.3 | 95.6 | 81.1 | 84.9 |
| 6.3 | 93.7 | 81.7 | 87.2 |
| 7.3 | 92.2 | 79.8 | 86.6 |

TABLE 19

(No. 3 catalyst of Reference example 7)

| time elapsed (hr) | cyclohexanone oxime conversion (%) | ε-caprolactam yield (%) | ε-caprolactam selectivity (%) |
|---|---|---|---|
| 1.3 | 100 | 81.6 | 81.6 |
| 2.3 | 99.5 | 82.0 | 82.4 |
| 3.3 | 97.4 | 82.5 | 84.7 |
| 4.3 | 95.5 | 81.3 | 83.5 |
| 5.3 | 93.2 | 80.0 | 85.8 |
| 6.3 | 92.0 | 80.3 | 87.3 |

EXAMPLE 15

(A test under high WHSV)

Example 12 was repeated except the catalyst used therein was calcined in a reactor at 500° C. for 3 hours in air stream, in place of the H.ZSM-5. Result is shown in Table 20.

TABLE 20

| time elapsed (hr) | cyclohexanone oxime conversion (%) | ε-caprolactam yield (%) | ε-caprolactam selectivity (%) |
|---|---|---|---|
| 1.3 | 99.0 | 72.1 | 72.9 |
| 2.3 | 97.6 | 74.5 | 76.3 |
| 3.3 | 96.1 | 77.5 | 80.6 |
| 4.3 | 94.2 | 76.3 | 81.0 |
| 5.3 | 92.3 | 74.0 | 80.2 |
| 6.3 | 91.0 | 73.1 | 80.3 |

REFERENCE EXAMPLE 8

ZSM-5s (NH$_4$ form) obtained in Reference example 7, No. 4 (4 g each) were subjected four times, at 90° C. for one hour each, to ion-exchange treatment with aqueous 5% solution (50 ml) of metal salt (MXn: X=Cl$^-$ or OAc$^-$) shown in Table 21, respectively. After washing with water, drying and calcining, metal ion-exchanged ZSM-5s were obtained.

TABLE 21

| Run No. | Metal salt | M.ZSM-5 |
|---|---|---|
| 1 | Ca(OAc)$_2$ | Ca.ZSM-5 |
| 2 | Sr(OAc)$_2$ | Sr.ZSM-5 |
| 3 | LaCl$_3$ | La.ZSM-5 |

EXAMPLE 16

(Test under high WHSV)

Example 1s were repeated except that metal ion-exchanged ZSM-5s prepared in Reference example 8 were used in place of the H.ZSM-5. Results are shown in Tables 22–24.

TABLE 22

(Ca.ZSM-5)

| time elapsed (hr) | cyclohexanone oxime conversion (%) | ε-caprolactam yield (%) | ε-caprolactam selectivity (%) |
|---|---|---|---|
| 1.3 | 99.1 | 71.4 | 72.0 |
| 2.3 | 97.6 | 73.4 | 75.2 |
| 3.3 | 96.0 | 76.8 | 80.0 |
| 4.3 | 93.8 | 75.1 | 80.1 |
| 5.3 | 92.0 | 73.9 | 80.3 |
| 6.3 | 90.1 | 72.1 | 80.0 |

TABLE 23

(Sr.ZSM-5)

| time elapsed (hr) | cyclohexanone oxime conversion (%) | ε-caprolactam yield (%) | ε-caprolactam selectivity (%) |
|---|---|---|---|
| 1.3 | 100 | 75.0 | 75.0 |
| 2.3 | 99.6 | 77.2 | 77.5 |
| 3.3 | 98.3 | 80.1 | 81.5 |
| 4.3 | 97.0 | 79.5 | 82.0 |
| 5.3 | 95.3 | 78.0 | 81.8 |
| 6.3 | 94.0 | 77.4 | 82.3 |

TABLE 24

(La.ZSM-5)

| time elapsed (hr) | cyclohexanone oxime conversion (%) | ε-caprolactam yield (%) | ε-caprolactam selectivity (%) |
|---|---|---|---|
| 1.3 | 99.3 | 70.3 | 70.8 |
| 2.3 | 97.0 | 71.0 | 73.2 |
| 3.3 | 95.8 | 75.3 | 78.6 |
| 4.3 | 94.0 | 73.1 | 77.8 |
| 5.3 | 92.5 | 70.8 | 76.5 |
| 6.3 | 90.3 | 69.5 | 77.0 |

REFERENCE EXAMPLE 9

Solutions defined below were prepared:

| Solution A | |
|---|---|
| Distilled water | 162 g |
| H$_2$SO$_4$ | 16.7 g |
| Al$_2$(SO$_4$)$_3$.17H$_2$O | 0.16 g |
| (n-Pr)$_4$NBr | 20.3 g |
| Solution B | |
| Distilled water | 119.7 g |
| Sodium silicate (JIS No. 3) | 186.3 g |
| Solution C | |
| Distilled water | 281.7 g |
| NaCl | 70.9 g |

To the solution C were dropped at the same time the solutions A and B. The mixture was vigorously stirred, keeping pH 9–11 with addition of aqueous 48% NaOH solution (6 g).

The mixture (pH 9.6) was charged in an autoclave (one l) made of SUS and stirred ($\geq$400 r.p.m.) at 160° C. for 20 hours to effect hydrothermal synthesis. After being cooled, the reaction mixture was repeatedly subjected to filtration and washing with a large amount (about 7 l) of distilled water until no Cl was detected. After the mixture was dried at 120° C. for 16 hours, BET surface area in external area was 18.3 m$^2$/g. The mixture was calcined at 500°–550° C. for 4 hours in air stream to obtain white powdery crystals (48 g) which were identified as ZSM-5 by X ray diffraction.

Ion-exchanging and calcining as same as in Reference example 1 were effected to obtain H.ZSM-5.

Surface acidity (pKa)= −3

4 MQ adsorption amount=3.62μ equivalent/g (350° C.)

Si/Al atomic ratio=550

EXAMPLE 17

(A test under high WHSV)

Example 1 was repeated except the H.ZSM-5 obtained in Reference example 9 was used in place of the H.ZSM-5. Result is shown in Table 25.

TABLE 25

| time elapsed (hr) | cyclohexanone oxime conversion (%) | ε-caprolactam yield (%) | ε-caprolactam selectivity (%) |
|---|---|---|---|
| 1.3 | 100 | 76.8 | 76.8 |
| 2.3 | 99.3 | 81.0 | 81.6 |
| 3.3 | 98.3 | 79.6 | 81.0 |
| 4.3 | 96.9 | 82.2 | 84.8 |
| 5.3 | 95.4 | 81.0 | 85.0 |
| 6.3 | 93.6 | 79.7 | 85.1 |

COMPARISON EXAMPLES 1-3

(Tests under high WHSV)

Example 1s were repeated except that H.ZSM-5s having various Si/Al atomic ratios of 7.9, 17.3 and 49.2 were used, respectively, in place of the H.ZSM-5. Results are shown in Tables 26–28.

TABLE 26

| | (Si/Al = 7.9) | | |
|---|---|---|---|
| time elapsed (hr) | cyclohexanone oxime conversion (%) | ε-caprolactam yield (%) | ε-caprolactam selectivity (%) |
| 1.3 | 60.0 | 26.3 | 43.8 |
| 2.3 | 37.3 | 14.5 | 38.9 |
| 3.3 | 30.5 | 10.1 | 33.1 |

TABLE 27

| | (Si/Al = 17.3) | | |
|---|---|---|---|
| time elapsed (hr) | cyclohexanone oxime conversion (%) | ε-caprolactam yield (%) | ε-caprolactam selectivity (%) |
| 1.3 | 66.0 | 24.4 | 37.0 |
| 2.3 | 25.8 | 10.1 | 39.1 |
| 3.3 | 8.9 | 4.1 | 46.0 |

TABLE 28

| | (Si/Al = 49.2) | | |
|---|---|---|---|
| time elapsed (hr) | cyclohexanone oxime conversion (%) | ε-caprolactam yield (%) | ε-caprolactam selectivity (%) |
| 1.3 | 68.5 | 34.3 | 50.1 |
| 2.3 | 24.1 | 13.2 | 53.4 |
| 3.3 | 14.3 | 7.7 | 53.8 |

EXAMPLE 18

A reactor made of quartz (32 cm long, 1 cm inner diameter) was packed with H.ZSM-5 catalyst (24–48 mesh in size, 0.6 g, 1.02 ml) prepared in Reference example 5, No. 1 and $N_2$ gas was passed therethrough at 350° C. for one hour. Cyclohexanone oxime solution (7.53 wt.%) in benzene was charged (WHSV=9.77 hr$^{-1}$) from a vaporizer. Temperature of a catalyst bed was 350° C.

Result is shown in Table 29.

TABLE 29

| time elapsed (hr) | cyclohexanone oxime conversion (%) | ε-caprolactam yield (%) | ε-caprolactam selectivity (%) |
|---|---|---|---|
| 2 | 100 | 75.0 | 75.0 |
| 3 | 100 | 78.5 | 78.5 |
| 4 | 100 | 77.1 | 77.1 |
| 5 | 100 | 78.7 | 78.7 |
| 6 | 100 | 78.0 | 78.0 |
| 7 | 100 | 79.2 | 79.2 |
| 8 | 100 | 80.6 | 80.6 |
| 9 | 100 | 82.8 | 82.8 |
| 10 | 100 | 81.5 | 81.5 |
| 11 | 100 | 81.2 | 81.2 |
| 12 | 100 | 82.5 | 82.5 |

EXAMPLE 19

The same reactor as in Example 18 was packed with H.ZSM-5 catalyst (0.6 g, 1.02 ml) prepared in Reference example 5, No. 1 and $N_2$ gas was passed through at 350° C. for one hour. Cyclohexanone oxime solution (7.7 wt.%) in benzene and $CO_2$ gas, a carrier, which had been mixed together were charged (WHSV=9.83 hr$^{-1}$ and 10 ml/min, respectively) from a vaporizer. Temperature of a catalyst bed was 350° C.

Result is shown in Table 30.

TABLE 30

| time elapsed (hr) | cyclohexanone oxime conversion (%) | ε-caprolactam yield (%) | ε-caprolactam selectivity (%) |
|---|---|---|---|
| 2.5 | 100 | 81.5 | 81.5 |
| 3.5 | 100 | 83.5 | 83.5 |
| 4.5 | 100 | 83.8 | 83.8 |
| 5.5 | 100 | 86.3 | 86.3 |
| 6.5 | 100 | 84.4 | 84.4 |
| 7.5 | 100 | 85.1 | 85.1 |
| 8.5 | 100 | 84.8 | 84.8 |
| 9.5 | 100 | 86.7 | 86.7 |
| 10.5 | 100 | 87.4 | 87.4 |
| 11.5 | 100 | 85.4 | 85.4 |
| 13.5 | 100 | 86.1 | 86.1 |
| 15.5 | 99.5 | 86.7 | 87.1 |
| 17.5 | 98.9 | 86.2 | 87.1 |
| 19.5 | 98.4 | 83.5 | 84.9 |
| 21.5 | 97.2 | 85.0 | 87.5 |
| 23.0 | 96.7 | 85.4 | 86.1 |

Extrapolation of data in Table 30 shows that half value period is about 150 hours.

EXAMPLE 20

Example 19 was repeated except that $N_2$ gas, a carrier, was employed in place of $CO_2$, and WHSV was 9.82 hr$^{-1}$ in place of 9.83 hr$^{-1}$.

Result is shown in Table 31.

TABLE 31

| time elapsed (hr) | cyclohexanone oxime conversion (%) | ε-caprolactam yield (%) | ε-caprolactam selectivity (%) |
|---|---|---|---|
| 1.3 | 100 | 75.9 | 75.9 |
| 2.3 | 100 | 76.8 | 76.8 |
| 3.3 | 100 | 77.8 | 77.8 |
| 4.3 | 100 | 78.4 | 78.4 |
| 5.3 | 100 | 81.1 | 81.1 |
| 7.3 | 100 | 80.2 | 80.2 |
| 8.5 | 100 | 83.2 | 83.2 |
| 9.5 | 100 | 84.0 | 84.0 |
| 10.5 | 100 | 82.8 | 82.8 |
| 11.5 | 100 | 82.2 | 82.2 |
| 13.5 | 100 | 82.0 | 82.0 |
| 14.5 | 100 | 82.5 | 82.5 |

EXAMPLE 21

The same reactor as in example 18 was packed with H.ZSM-5 catalyst (0.6 g, 1.02 ml) prepared in Reference example 7, No. 1 and $N_2$ gas was passed through at 350° C. for one hour. Cyclohexanone oxime solution (8.0 wt.%) in benzene was charged (WHSV=10.8 hr$^{-1}$) from a vaporizer. Temperature of a catalyst bed was 350° C.

Result is shown in Table 32.

TABLE 32

| time elapsed (hr) | cyclohexanone oxmie conversion (%) | ε-caprolactam yield (%) | ε-caprolactam selectivity (%) |
|---|---|---|---|
| 1.3 | 100 | 73.4 | 73.4 |
| 2.3 | 100 | 76.7 | 76.7 |
| 3.3 | 100 | 79.7 | 79.7 |
| 4.3 | 100 | 81.0 | 81.0 |
| 5.3 | 100 | 83.9 | 83.9 |
| 6.3 | 100 | 84.2 | 84.0 |

TABLE 32-continued

| time elapsed (hr) | cyclohexanone oxmie conversion (%) | ε-caprolactam yield (%) | ε-caprolactam selectivity (%) |
|---|---|---|---|
| 8.0 | 100 | 86.6 | 86.6 |
| 9.0 | 100 | 88.8 | 88.8 |
| 10.0 | 100 | 87.2 | 87.2 |
| 11.0 | 100 | 86.5 | 86.5 |
| 12.0 | 100 | 86.1 | 86.1 |
| 13.0 | 100 | 85.9 | 85.9 |
| 14.0 | 100 | 88.8 | 88.8 |

EXAMPLE 22

Example 21 was repeated except that, in place of stopping the reaction after 14 hours, the reaction was continued thereafter by charging $CO_2$ gas, a carrier, (10 ml/min) after 14.5 hours was elapsed since the reaction began.

Result is shown in Table 33.

TABLE 33

| time elapsed (hr) | cyclohexanone oxime conversion (%) | ε-caprolactam yield (%) | ε-caprolactam selectivity (%) |
|---|---|---|---|
| 15.5 | 100 | 90.5 | 90.5 |
| 16.5 | 100 | 90.0 | 90.0 |
| 17.5 | 100 | 91.6 | 91.6 |
| 18.3 | 99.6 | 90.2 | 90.6 |
| 19.3 | 99.5 | 90.1 | 90.6 |
| 20.3 | 99.3 | 89.9 | 90.5 |
| 23.0 | 98.6 | 88.7 | 90.0 |
| 24.0 | 97.7 | 89.2 | 91.3 |
| 25.0 | 97.3 | 86.8 | 89.2 |
| 26.0 | 96.5 | 87.9 | 91.1 |
| 27.0 | 95.6 | 86.0 | 90.0 |
| 28.0 | 95.0 | 85.7 | 90.2 |
| 29.0 | 93.9 | 86.2 | 91.9 |

Extrapolation of conversion rate shows that half value period of catalyst activity, i.e., a period until conversion rate is lowered to 50% is about 120 hours.

EXAMPLE 23

Example 21 was repeated except that H.ZSM-5 prepared in Reference example 7, No. 4 was used in place of the H.ZSM-5.

Result is shown in Table 34.

TABLE 34

| time elapsed (hr) | cyclohexanone oxime conversion (%) | ε-caprolactam yield (%) | ε-caprolactam selectivity (%) |
|---|---|---|---|
| 0.3–1.3 | 100 | 81.1 | 81.1 |
| 2.3 | 100 | 85.5 | 85.5 |
| 3.3 | 99.6 | 85.5 | 85.9 |
| 4.3 | 99.2 | 86.0 | 86.7 |
| 5.3 | 98.7 | 85.7 | 86.9 |
| 6.3 | 98.0 | 83.8 | 85.5 |
| 7.3 | 97.1 | 85.3 | 87.9 |
| 8.3 | 96.4 | 82.5 | 85.6 |
| 9.3 | 95.7 | 82.4 | 86.1 |
| 10.3 | 94.9 | 80.9 | 85.3 |
| 11.3 | 94.2 | 81.0 | 86.0 |
| 12.3 | 93.5 | 80.6 | 86.2 |
| 13.3 | 92.7 | 79.4 | 85.7 |
| 14.3 | 92.0 | 78.4 | 85.2 |
| 15.3 | 91.1 | 78.4 | 86.1 |
| 16.3 | 90.3 | 78.4 | 86.8 |

COMPARISON EXAMPLE 4

Example 21 was repeated except that H.ZSM-5 having 49.2 of Si/Al atomic ratio in place of the H.ZSM-5. Result is shown in Table 35.

TABLE 35

| time elapsed (hr) | cyclohexanone oxime conversion (%) | ε-caprolactam yield (%) | ε-caprolactam selectivity (%) |
|---|---|---|---|
| 1.3 | 80.5 | 42.7 | 53.0 |
| 2.3 | 75.0 | 43.6 | 58.2 |
| 3.3 | 68.7 | 42.0 | 61.1 |
| 4.3 | 62.5 | 40.0 | 64.0 |
| 5.3 | 55.2 | 36.2 | 65.5 |
| 6.3 | 47.3 | 31.1 | 65.7 |

COMPARISON EXAMPLE 5

Example 18 was repeated except that silica-alumina catalyst (0.6 g, alumina 26%, manufactured by Shokubai Kasei Co. Ltd.) was used in place of the H.ZSM-5. Result is shown in Table 36.

TABLE 36

| time elapsed (hr) | cyclohexanone oxime conversion (%) | ε-caprolactam yield (%) | ε-caprolactam selectivity (%) |
|---|---|---|---|
| 2 | 100 | 56.1 | 56.1 |
| 3 | 100 | 58.9 | 58.9 |
| 4 | 100 | 57.5 | 57.5 |
| 5 | 100 | 58.9 | 58.9 |
| 6 | 100 | 61.0 | 61.0 |
| 7 | 100 | 61.6 | 61.6 |
| 8 | 100 | 61.3 | 61.3 |
| 9 | 100 | 64.2 | 64.2 |
| 10 | 100 | 61.6 | 61.6 |
| 11 | 100 | 65.1 | 65.1 |
| 12 | 100 | 64.8 | 64.8 |

COMPARISON EXAMPLE 6

Example 18 was repeated except B$_2$O$_3$/ZnO catalyst (30/70 wt.%, 0.6 g) was used in place of the H.ZSM-5. Result is shown in Table 37.

TABLE 37

| time elapsed (hr) | cyclohexanone oxime conversion (%) | ε-caprolactam yield (%) | ε-caprolactam selectivity (%) |
|---|---|---|---|
| 2 | 100 | 98.0 | 98.0 |
| 3 | 97.5 | 92.8 | 95.2 |
| 4 | 95.1 | 85.9 | 90.3 |
| 5 | 92.0 | 81.4 | 88.5 |
| 6 | 88.4 | 76.9 | 87.0 |
| 7 | 81.7 | 67.5 | 82.6 |
| 8 | 74.3 | 59.0 | 79.4 |
| 9 | 65.9 | 49.6 | 75.3 |
| 10 | 54.1 | 39.2 | 72.5 |
| 11 | 47.6 | 31.4 | 66.0 |
| 12 | 35.2 | 20.8 | 59.3 |

We claim:

1. A method for preparing ε-caprolactam which comprises bringing cyclohexanone oxime in a gaseous phase into contact with crystalline alumino-silicate catalyst having 1–12 of constraint index, 500 or more of Si/Al atomic ratio and 5μ equivalent/g or less of external acid amount.

2. A method according to claim 1 wherein the alumino-silicate has 5 m$^2$/g or more of external surface area.

3. A method according to claim 1 wherein the alumino-silicate is ZSM-5, ZSM-11, ZSM-23 or Silicalite.

4. A method according to claim 1 wherein Si/Al atomic ratio of the alumino-silicate is 1000 or more.

5. A method according to claim 1 wherein external acid amount of the alumino-silicate is $2\mu$ equivalent/g or less.

6. A method according to claim 1 wherein the alumino-silicate is in $H^+$ form.

7. A method according to claim 1 wherein the alumino-silicate is one which has been ion-exchanged with alkaline-earth metal or lanthanoide metal.

8. A method according to claim 1 wherein the cyclohexanone oxime is diluted one with benzene or toluene.

9. A method according to claim 1 wherein the cyclohexanone oxime is fed at 1–50 $hr^{-1}$ in terms of WHSV.

10. A method according to claim 9 wherein WHSV is 5–40 $hr^{-1}$.

11. A method according to claim 1 wherein the cyclohexanone oxime is fed with inert gas as a carrier.

12. A method according to claim 1 wherein the contact is made at a temperature of 300°–450° C.

13. A method for preparing $\epsilon$-caprolactam comprising:
bringing cyclohexanone oxime in a gaseous phase into contact with a crystalline alumino-silicate catalyst having a constraint index of 1–12, a Si/Al atomic ratio of at least 1,000, an external surface area of at least 5 $m^2/g$, and $5\mu$ equivalents/g or less of external acid amount, said cyclohexanone oxime being fed at 1–50 $hr^{-1}$ in terms of WHSV.

14. The method according to claim 13 wherein the alumino-silicate is ZSM-5, ZSM-11, ZSM-23 or Silicalite.

* * * * *